(12) United States Patent
Stuck et al.

(10) Patent No.: US 8,626,672 B2
(45) Date of Patent: Jan. 7, 2014

(54) SECURE TRACKING OF TABLETS

(75) Inventors: Alexander Stuck, Wettingen (SE);
Stefan Klocke, Karlsruhe (DE); Harald Walter, Zurich (SE)

(73) Assignee: I-Property Holding Corp., Sarasota, FL (US)

( * ) Notice: Subject to any disclaimer, the term of this patent is extended or adjusted under 35 U.S.C. 154(b) by 79 days.

(21) Appl. No.: 12/841,649

(22) Filed: Jul. 22, 2010

(65) Prior Publication Data
US 2011/0091068 A1    Apr. 21, 2011

Related U.S. Application Data

(63) Continuation-in-part of application No. PCT/US2009/051528, filed on Jul. 23, 2009.

(60) Provisional application No. 61/082,998, filed on Jul. 23, 2008, provisional application No. 61/227,826, filed on Jul. 23, 2009.

(51) Int. Cl.
*G06Q 99/00* (2006.01)
*G06Q 30/00* (2012.01)
*G03H 1/00* (2006.01)

(52) U.S. Cl.
CPC ......... *G06Q 30/0185* (2013.01); *G03H 1/0011* (2013.01)
USPC ................ 705/318; 359/2; 235/375; 382/141

(58) Field of Classification Search
CPC ........................ C03H 1/0011; G06Q 30/0185
USPC ................ 382/141; 235/375; 359/2; 705/318
See application file for complete search history.

(56) References Cited

U.S. PATENT DOCUMENTS

| | | | |
|---|---|---|---|
| 4,668,523 A | 5/1987 | Begleiter |
| 5,502,944 A | 4/1996 | Kraft et al. |
| 5,700,998 A | 12/1997 | Palti |
| 5,845,264 A | 12/1998 | Nellhaus |
| 5,992,742 A | 11/1999 | Sullivan et al. |
| 6,505,461 B1 | 1/2003 | Yasunaga |
| 6,543,692 B1 | 4/2003 | Nellhaus et al. |
| 6,771,369 B2 | 8/2004 | Rzasa et al. |

(Continued)

FOREIGN PATENT DOCUMENTS

| | | |
|---|---|---|
| WO | 03005839 A2 | 1/2003 |
| WO | 2006/047695 A2 | 5/2006 |
| WO | 2007/137438 A1 | 12/2007 |

OTHER PUBLICATIONS

Zeitler et al., "In-vitro Tomography and Non-Destructive Imaging at Depth of Pharmaceutical Solid Dosage Forms", Jul. 18, 2008, 32 pgs.*

(Continued)

*Primary Examiner* — Ryan Zeender
*Assistant Examiner* — Hunter Wilder
(74) *Attorney, Agent, or Firm* — Wood, Herron & Evans, LLP

(57) ABSTRACT

A method of tracking and tracing tablets, in particular pharmaceutical tablets, includes reading, i.e. detecting, code structure from the tablet, reading additional information from the package on an information sheet, and then comparing the readings to verify authenticity. The code structure may be two-dimensional or three-dimensional. The detected code may further be compared with information stored in a database.

5 Claims, 2 Drawing Sheets

(56) References Cited

U.S. PATENT DOCUMENTS

| | | | |
|---|---|---|---|
| 6,776,341 | B1 | 8/2004 | Sullivan et al. |
| 7,136,539 | B2 | 11/2006 | Weyl |
| 7,218,395 | B2 | 5/2007 | Kaye et al. |
| 7,770,732 | B2 | 8/2010 | Stroppolo et al. |
| 7,889,330 | B2 | 2/2011 | Newcomb |
| 2005/0261937 | A1 | 11/2005 | Silverbrook et al. |
| 2006/0068006 | A1 | 3/2006 | Begleiter |
| 2006/0091208 | A1 | 5/2006 | He et al. |
| 2006/0206714 | A1 | 9/2006 | Gubo |
| 2006/0226234 | A1 | 10/2006 | Kettinger et al. |
| 2007/0086625 | A1 | 4/2007 | Polli et al. |
| 2007/0190133 | A1 | 8/2007 | Bunick et al. |
| 2007/0199991 | A1 | 8/2007 | Haraszti et al. |
| 2007/0219916 | A1 | 9/2007 | Lucas |
| 2007/0241177 | A1* | 10/2007 | Tuschel et al. ............ 235/375 |
| 2007/0286811 | A1 | 12/2007 | Walter |
| 2008/0042843 | A1 | 2/2008 | Kim |
| 2008/0199406 | A1* | 8/2008 | Walter et al. ............ 424/10.2 |
| 2009/0159174 | A1* | 6/2009 | Grimard ............ 156/64 |
| 2010/0046825 | A1 | 2/2010 | Haushalter |
| 2010/0110514 | A1 | 5/2010 | Houha et al. |
| 2010/0143467 | A1 | 6/2010 | Stuck et al. |
| 2010/0294927 | A1* | 11/2010 | Nelson et al. ............ 250/307 |
| 2011/0026010 | A1* | 2/2011 | Walker ............ 356/51 |
| 2011/0091068 | A1 | 4/2011 | Stuck et al. |

OTHER PUBLICATIONS

International Search Report of PCT/US2009/51528, U.S. Patent and Trademark Office, Sep. 22, 2009.
European Patent Office, International Search Report, Form PCT/ISA/210 (3 pgs.), and Written Opinion, Form PCT/ISA/237 (5 pgs.), Apr. 1, 2011, for PCT/US2011/22065.
The International Bureau of WIPO, International Preliminary Report on Patentability, Apr. 23, 2013, for counterpart International Patent Application No. PCT/2011/022065. (6 pages).
European Patent Office, International Search Report issued in International Patent Application No. PCT/US2011/22065 and Written Opinion, dated Apr. 1, 2011, (8 pages).
U.S. Patent and Trademark Office, International Search Report issued in International Patent Application No. PCT/US2009/51528, dated Sep. 22, 2009, (7 pages).
European Patent Office, International Search Report and Written Opinion, issued in International Patent Application No. WO 2009/051805 (also PCT/US2008/011889) dated Feb. 10, 2009, (8 pages).
U.S. Patent and Trademark Office, Non-final Office Action issued in U.S. Appl. No. 13/010,510, dated May 3, 2013, (17 pages).
U.S. Patent and Trademark Office, Non-final Office Action issued in U.S. Appl. No. 13/010,101, dated Aug. 1, 2013, (10 pages).
U.S. Patent and Trademark Office, Final Office Action issued in U.S. Appl. No. 13/010,101, dated Feb. 14, 2013, (11 pages).
U.S. Patent and Trademark Office, Non-final Office Action issued in U.S. Appl. No. 13/010,101, dated Jul. 18, 2012, (10 pages).
U.S. Patent and Trademark Office, Non-final Office Action issued in U.S. Appl. No. 13/010,101, dated Mar. 5, 2012, (8 pages).

* cited by examiner

SECURE TRACKING OF TABLETS

RELATED APPLICATION

This application claims priority to International Application No. PCT/US2009/51528, filed Jul. 23, 2009, which claims priority to U.S. Ser. No. 61/082,998, filed Jul. 23, 2008. This application also claims priority to U.S. Ser. No. 61/227,826, filed Jul. 23, 2009. Each of these prior applications is incorporated herein by reference, in its entirety

FILED OF INVENTION

This invention relates to the tracking of pharmaceutical tablets, to verify authenticity.

BACKGROUND OF THE INVENTION

Pharmaceuticals and cosmetics are high technology products which require very specialized material systems and production procedures as well as very large investments in development and marketing. Because of public safety concerns, authorities place very stringent requirements on the verification and authenticity of such products. Companies therefore have to make huge investments in the tracking and tracing of these products to ensure authenticity. In addition, as these products usually have large sales margins and are distributed globally, it is not surprising that cosmetics manufacturers and pharmaceutical companies suffer from enormous losses due to counterfeiting. The problem has been aggravated by strongly increased sales over the internet, where everything from counterfeit Viagra to false glucose tests is readily available.

Track-and-trace features in the pharmaceutical market have been applied to packages. For example, holograms, optically variable inks, fluorescent dyes, and other identification features are attached to the packages, e.g., by adhesive tags. Alternatively, such labels are laminated to the carton or are directly applied to the packages. The main drawback of such labels is that they are not an integral part of the tablet and therefore do not provide 100% security. For example, if the authentic product is separated from the package, the package can be refilled with a false product. Therefore, direct verification of an authentic tablet, and ensuring that the authentic tablet is in the correct package, remains a primary concern.

Although there are some known approaches for secure labelling of the tablets themselves, each suffers from one or more drawbacks.

For instance, techniques based on forgery-resistant signatures, such as DNA of known sequence (U.S. Pat. No. 5,451, 505) or molecules with characteristic isotopic composition or micro-particles with characteristic colour layer sequence (U.S. Pat. No. 6,455,157 B1), are considered unsuitable for pharmaceutical tablets, as these signatures are administered simultaneously and require additional regulatory approval.

WO2006/027688A1 describes an article, such as a tablet, having a visible diffractive microstructure on its surface or at an interface. Illuminated with white light, the tablet shows a rainbow colour effect similar to holograms. The diffractive microstructure can provide an indication of authenticity of the tablet. Although suitable for verification purposes, that document discloses a security element that is visible to the unaided eye. This visibility can tip off counterfeiters. Second, it is difficult to encode a large amount of data in such diffractive microstructures, and to do so consistently.

EP1958620A1 teaches a verification method based on three-dimensional structures such as barcodes or logos impressed or embossed in tablets, in particularly pharmaceutical tablets. Further methods to manufacture tablet compression tools are disclosed. This patent application is incorporated in its entirety.

A number of optical detection devices useful for analysing three-dimensional structures are known. White light interferometers are state of the art but operate rather slowly. Optical coherence tomography (OCT) is another known technique capable of visualising three dimensional patterns, even if they are located at an interface below the surface of an article. The depth that can be visualised in a material depends on the optical properties of the material. It can be up to a few millimetres at present. U.S. Pat. No. 6,469,489 describes an array sensor which is used for parallel optical low-coherence tomography (pOCT) which enables real-time 3D imaging for topographic pattern. It provides fast, three-dimensional and structural information with spatial resolution in the micrometer range. A plurality of electrical detection circuits with parallel outputs can form a one-dimensional or two-dimensional array sensor for the coherent or heterodyne analogue detection of intensity modulated optical signals simultaneously for all pixels with a high dynamic range. The array sensor may be used, e.g., for optical 3D measurements, and especially in optical low-coherence tomography. It is known to use OCT for investigating the human skin, to control the quality of fast production processes (e.g., in die-bonding), in SMD pick-and-place systems, as well as in mechanical inspection systems. Variants of these detection techniques do not use interferometry, but time-modulated optical signals to provide accurate 3D measurements of objects. Such variants often use parallel processing of lock-in signals on a single chip to provide fast and accurate distance information to an object. One example is time-of-flight (TOF) or related methods, where infrared or visible light from a camera's internal lighting source is time modulated and reflected by objects in the scene. It travels back to the camera, where its time of arrival is measured independently by each pixel on a sensor array or chip. In contrast to conventional cameras, such cameras provide a complete distance map of all objects in the field of view on a pixel-by-pixel basis.

BRIEF SUMMARY OF THE INVENTION

Altogether, there exists a need to verify the authenticity of tablets, in a manner that is contactless, fast, and reliable, and preferably also in a way that travels with the tablet.

Thus, it is an object of the present invention to mitigate at least some of the drawbacks of the state of the art relative to verifying the authenticity of tablets. In particular, it is an aim of the present invention to track and trace tablets through the production and supply chain, by marking the tablets themselves with a two- or three-dimensional code, for instance by embossing or impressing, and linking the code to information on the package or a package insert, in order to reduce false delivery. The two- or three-dimensional code essentially comprises tracking information that does not change the composition and the production process of the tablet, and that can easily be read. Further, it is an aim of the present invention to provide a fast, optical verification method for tablets and a system using that method to determine the authenticity of such tablets, while avoiding the drawbacks of known verification methods.

More particularly, the present invention relates to a track-and-trace method of tablets, namely pharmaceutical tablets wherein predetermined two- or three-dimensional code structures are formed in the tablets and are readable or detectable by an optical device, for example by optical coherence tomography (OCT). These coded structures are compared with information carrying structures or features on the package or on an information sheet placed in the package. Optionally, the information of the code structure is compared with data in a database.

The present invention is described in more detail below. It is to be understood that the various embodiments, preferences and ranges are subject to a reasonable amount of variation and interchangeability. Further, depending on the specific embodiment, it is possible that one or more of the selected definitions, embodiments, or ranges that are described herein may not apply in certain circumstances.

Unless otherwise stated, the following definitions apply in this specification:

The terms "tablet" or "pill" are known in the field. They relate in particular to a single solid dosage form comprising at least one solid active ingredient and optionally solid excipients (such as binders and other components). Tablets are usually manufactured by compacting, e.g., pressing, powders or granules of the respective components. The term "active ingredient" ("a.i."), as used herein, is not limited to a "pharmaceutical active ingredient" but includes all kinds of ingredients that are active, such as flavours, fragrances, active ingredients for animal health, active ingredients for plant protection etc. Further, tablets may be coated, resulting in a tablet comprising a core and coating. Tablets are usually intended to be swallowed, or dissolved in water and are therefore of a suitable size and shape for the purposes of the disclosed invention.

An "element of authenticity" or "topography pattern" comprises one or more predetermined three-dimensional structures. Its presence proves authenticity of a tablet or pill. Suitable structures are for example 2- or 3-dimensional bar codes, such as data matrix or pharma code, logos, symbols and the like.

A "predetermined three-dimensional structure" denotes any structure detectable by an optical device that can be measured and produced with an accuracy of better than 50 micros, preferred better than 10 microns.

A "verification method" is a method, preferred an optical method, that allows distinguishing genuine articles, such as tablets or pills, from false articles.

Also, in the context of "reading" information or code, the specification also uses the word "detecting."

BRIEF DESCRIPTION OF THE DRAWINGS

The Figures embedded within this specification are intended to further illustrate the invention.

DETAILED DESCRIPTION OF THE INVENTION

Figure 1:
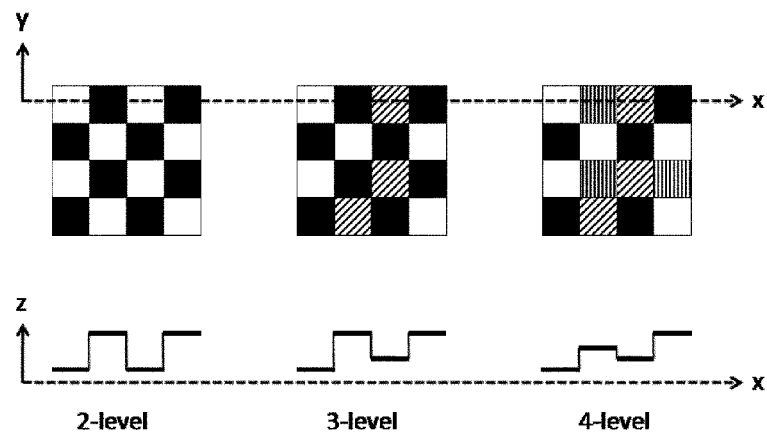
FIG. 1 shows a 4×4 matrix code with different depth levels.

FIG. 1 shows an example of a 4×4 matrix code with different depth levels. The x/y denotes the plane of the surface or interface of the tablet, and z is the perpendicular direction to this plane. 2-level: for example, normal black/white 2D bar code, 3-level: same code as 2-level code but additional third level contains a security code for authentication of the structure. 4-level: same as 2-level, but level 3 and 4 allow storage of additional product information on the same surface, like the 2-level code.

The invention relates to a track and trace method for tablets or a pills comprising at least one two- or- three-dimensional code structure on its surface or below a coating. Preferred the two- or- three-dimensional code structure is predetermined, wherein the smallest feature of the predetermined code structure is in the range of 10 µm up to 1 mm in lateral direction and >1 µm but <1 mm in vertical direction. The whole code structure itself has typically a lateral dimension $1d_{code}$ of 50 µm×50 µm up to 10 mm×10 mm. Its shape is not necessarily square. Other shapes are possible as well. The code structure may carry information about the tablet, such as the name, the type of tablet, ingredients, date of production, etc. Suitable, preferred and especially preferred lateral and vertical structure sizes of the predetermined code structure are listed in table 1:

|  | suitable range | preferred range | especially preferred range |
| --- | --- | --- | --- |
| $ld_{code}$ | 50 µm × 50 µm up to 10 mm × 10 mm | 500 µm × 500 µm up to 5 mm × 5 mm | 1000 µm × 1000 µm up to 2 mm × 2 mm |
| $s_{code}$ | 10 µm up to 1 mm | 30 µm up to 500 µm | 80 µm up to 300 µm |
| $h_{code}$ | 1 µm up to 1 mm | 2 µm up to 500 µm | 5 µm up to 50 µm |

In an advantageous embodiment, the optical detection device is capable of measuring 3D topologies. In this case the information of the code is built into the depth profile of the code structure as well as the lateral distribution of the code structure.

In a further advantageous embodiment, the optical detection device is an optical 3D camera which uses time-modulated optical signals to accurately measure depth, such as an optical coherence tomography, optical time of flight, or similar device.

The term tablet is known in the field and already defined above. Some tablets consist of nearly 100% active ingredient (a.i.). Aspirin is one such example. Typically, a tablet is a mixture of at least one active ingredient and excipients, usually in powder or granulated form, pressed into a solid dosage form. The mixtures consist of particles of different size, whereas the particle size distribution is considered critical for the compression process. A typical composition of such a powder mixture which is suitable for pharmaceutical tablets comprises 50-80% of a Lactose derivative (e.g. 73% Lactose Monohydrate), 10-50% of a cellulose derivative (e.g., 24% Microcrystalline Cellulose), 0.1-5% Silica, (e.g., 1% Aerosil (colloidal silica, anhydrous)), 0.1-5% of a fatty acid salt (e.g. 1% Magnesium-stearate) and 0.1-20% of a.i. (e.g., 1% a.i.). Lactose and cellulose are the most widely used binding and filling agents, Aerosil improves the powder flow, and Mg-stearate is used as a lubricant. The particle size distribution of the powder is usually 15-25% smaller than 75 µm, 30-50% in the range of 75 µm-150 µm, 15-25% between 150 µm-250 µm, 5-15% between 250 µm-500 µm and less than 2% larger than 500 µm.

The tablet may comprise a pharmaceutically active ingredient ("pharmaceutical tablet" or "pill"). Pills are in particular subject to counterfeiting, and authentication devices are therefore of particular relevance.

The predetermined two- or three-dimensional code structure may be any structure and is not limited to any periodicity or particular shape. Suitable are for example, alphanumeric characters, geometric figures, bar codes, in particular pharma code and data matrix code, logos, or combinations thereof. The three-dimensional code structure may be either an impression or a ridge or both; preferred are impressed three-dimensional structures.

Preferred the predetermined three-dimensional code structure is 50 µm to 5 mm in both lateral directions and 2 µm to 800 µm in vertical direction. These structures may possess two vertical levels or more (see FIG. 1). Structures of this size are detectable by an optical detection device and can be visible or invisible to the unaided eye. Such tablets are easy to manufacture, fully comply with existing manufacturing processes, and can be distinguished from false products, e.g., by a method as described below.

The two- or three dimensional code structures in the pill or tablet may be located in a macroscopic depression of the pill or tablet such as macroscopic letters or logos and the like. By doing so the structures are protected from being abraded by e.g. mechanical contacts of tablets during the production process or by de-powdering processes and the like. The code structures can be embossed or impressed in the cross of the logo of the company Bayer as it is used on Aspirin® tablets for instance.

In a first aspect, the invention relates to a verification and track-and-trace method for a tablet wherein the tablet comprises one or more two- or three-dimensional code structures on its surface or below a coating. The code structure is visible or invisible to the unaided eye. The method comprises detecting the code structure by an optical detection device and comparing the detected information, i.e., the code structure, with other information such as information which is encoded in information carrying structures or features on the package or on the information sheet in the package. Optionally, the information may be compared to data saved in a database. The two- or three-dimensional code structure may be a predetermined structure. Alternatively, the two- or three-dimensional structure may be the structure obtained by a state-of the art manufacturing process for tablets, the fingerprint of the tablet pressing tool or tools. The information from the tablet is read by an optical verification device, preferably capable of measuring three-dimensional topologies with a depth resolution of better than 30 microns within less than 8 seconds and verified electronically.

In an advantageous embodiment, the data encoded in the code structure on the tablet or pill is read by the verification device through the package, for example through a blister or a glass tube. The package itself may contain embossed and/or printed additional code structures which are read by the same or a second device. The device then compares the code on the package with the code on the tablet and cross-verifies both with each other.

Figure 2:
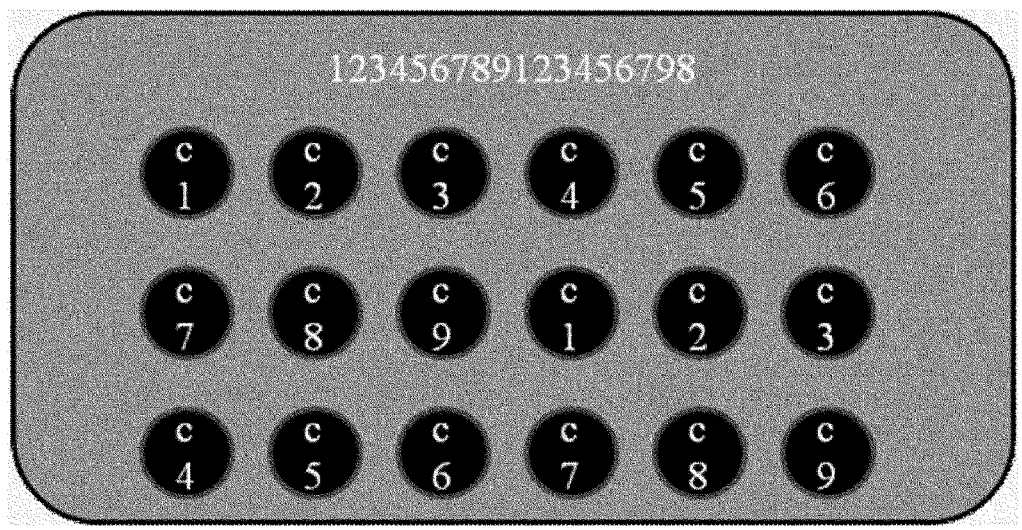
FIG. 2 shows an example of 18 tablets or pills packaged within a blister.

In still another embodiment at least two (or more) different code structures are present on tablets or pills within the same package. This can be realised easily by using in the production run tablet compressing tools with different code structures in the tool surface. If in a rotary press for example 64 compressing units are used and each of them manufactures tablets or pills with different code structures on average only every $64^{th}$ tablet or pill has the same code. If tablets or pills of such a production batch are packaged this inserts a degree of randomness in the package which can constitute a random code within itself. This random code generated by the geometrical arrangement of all tablets or pills in a package—for example within a blister—can be also read by the verification device and either be compared to a printed or embossed code on the blister or with a database for verification. FIG. 2 illustrates this based on an example with tablets with nine different code structures.

FIG. 2 shows an example of 18 tablets or pills packaged within a blister. Each tablet or pill contains a machine readable code c1-c9 (in this particular case). This code arrangement remains fixed in the supply chain and can be used for verification of the package. Each code c1-c9 on a pill can be different from the others or equal. The correct sequence of the security codes c1-c9 of this particular package might also be printed on the blister and used for cross verification of the package. Alternatively the pattern might be verified by comparison with an external database.

In an advantageous embodiment, the three-dimensional code structure contains a 1-, 2-, or 3-dimensional bar code, such as, but not limited to, a pharma or data matrix code. This code is read by an optical verification method as described above and compared to one or several additional data sets for verification. These additional data sets may also be, but do not have to be, on the pill or tablet or on the package of the pill. For example a step index code embossed into the pill with three or more distinguished height levels can contain several linked datasets; at most each level is a dataset of its own.

In a further advantageous embodiment, the additional data set is printed and/or embossed in/on the package of the pill, such as a blister, box, bottle, etc. Alternatively a label comprising the data set is stick to the package or it is applied by hot-transfer or lamination. The additional data set on the package is then compared with the data set from the pill or tablet to provide verification. For example, part of the data set on the pill contains a private cryptographic key that is used to unlock encrypted information on the additional data set on the package of the pill, or vice versa. In this way the system ensures that the pill actually is packed into the correct package, limiting the need to access external databases. To enhance security of the system, all data sets (on the package and on the pill) may be encrypted and be decrypted by the verification device before comparing and verifying the codes. In the case of a transparent and/or semitransparent package, such as a blister or bottle, this embodiment allows verification of the pill or tablet without opening the package (see FIG. 3). The method creates a direct link between the physical structure of the pill and information printed and/or embossed or otherwise marked on the package of the pill.

Figure 3A:
FIG. 3 shows a pOCT measurement of a datamatrix code impressed in the surface of a pharmaceutical tablet.
Figure 3B:

FIG. 3 shows a pOCT measurement of a datamatrix code of $1.6 \times 1.6 \ \mu m^2$ size impressed in the surface of a pharmaceutical tablet measured in air (a) and through a plastic transparent blister package (b). White denotes areas with impressed level in z-direction, while black denotes the surface of the tablet.

In a further advantageous embodiment, the additional data as well as encryption and description codes are stored in the verification device itself for verification.

Suitable optical detection devices are known in the field. In principle, any optical detection device capable of detecting three-dimensional structures as defined above is suitable. Preferred devices are selected from the class consisting of optical interferometry microscopes and time-modulated 3D cameras. They provide fast, three-dimensional and structural information with spatial resolution in the micrometer range. A plurality of electrical detection circuits with parallel outputs can form a one-dimensional or two-dimensional array sensor for the coherent or heterodyne analogue detection of intensity modulated optical signals simultaneously for all pixels with a high dynamic range. The array sensor may be used, e.g., for optical 3D measurements, and especially in optical low-coherence tomography. Variants of these detection techniques do not only use time domain interferometry, but other time-modulated optical signals to provide accurate 3D measurements of objects. Such variants often use parallel processing of lock-in signals on a chip to provide fast and accurate distance information to an object. One example is by time-of-flight (TOF) or related methods, where infrared or visible light from a camera's internal lighting source is time modulated and reflected by objects in the scene. It travels back to the camera, where its time of arrival is measured independently by each pixel on a sensor array or chip. In contrast to conventional cameras, such cameras provide a complete distance map of all objects in the field of view on a pixel-by-pixel basis.

A portable or fixed verification system may combine several of the above-mentioned 3D measuring systems as well as standard 2D camera systems to verify the embossed code simultaneously or in a fast time sequence on the pill and/or on the pill and the package of the pill.

As the described secure marking or information is also used for tracking and product tracing, a verification method is needed. Such method is preferably fast (i.e., it takes less than one second to distinguish forged from unique tablets and read the information on the tablet).

In a further advantageous embodiment, the invention relates to a verification method as described above wherein said tablet comprises a core and a coating and wherein said predetermined structure is located at an interface between said core and said coating and wherein said method comprises the step of detecting said structure through said coating. To apply the verification method to a coated tablet is considered particularly useful. Coated tablets are predominant on the market; the three-dimensional structure is protected against abrasion.

In a further advantageous embodiment, the invention relates to a verification method as described herein wherein said tablet is located in a blister. In this embodiment, verification of tablets takes place without unpacking the tablets. Blisters are typical packages for tablets, in particular pharmaceutical tablets. Thus, spot tests at distributors or pharmacies and the like are possible.

In a further advantageous embodiment, the invention relates to a verification method as described herein wherein said tablet is located in a blister and said optical detection device is a OCT, especially a pOCT. OCT is a suitable detection method, as standard blister packages are transparent in the visible to NIR region (typically between 400 and 900 nm). Therefore even packaged tablets can be verified by OCT.

In a further advantageous embodiment, the invention relates to a verification method for a tablet (in particular a tablet as defined herein) comprising the step of analysing (detecting and recording) said tablet by means of optical interference microscopy and comparing the obtained data set with a predefined data set.

Figure 4:
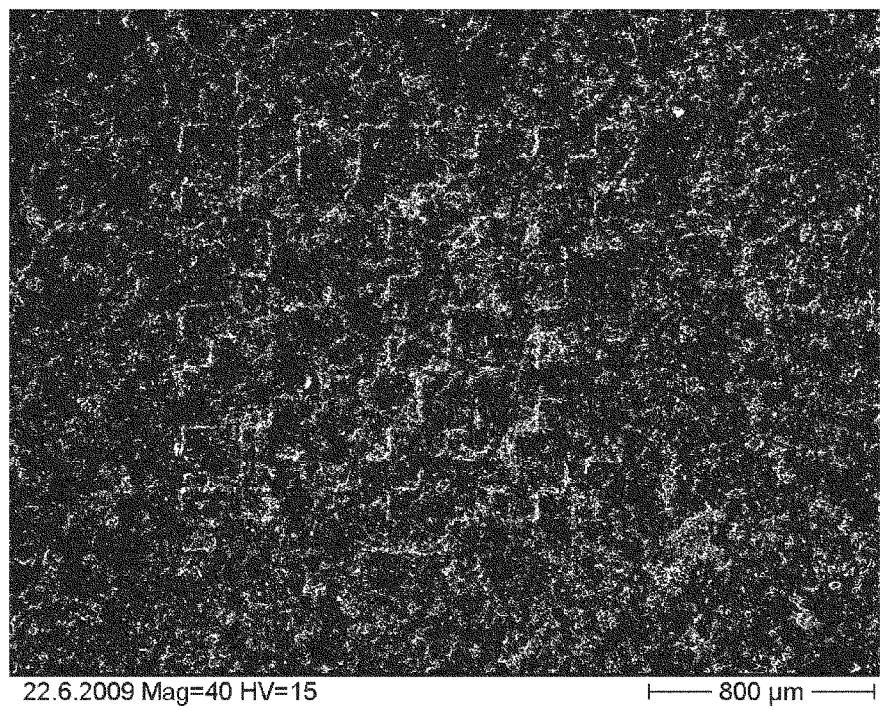
FIG. 4 shows a scanning electron microscopy picture of a pharmaceutical tablet with a datamatrix code structure impressed in the surface.

As the size of the powder particles of the tablet is predominantly in the range of 75 μm-500 μm the topography structure is superimposed on the grain structure of the particles. This has to be taken into account for the verification of the topography structure. FIG. 4 shows the grainy surface of a pharmaceutical tablet with a datamatrix code structure impressed in that surface. The picture was taken by scanning electron microscopy (SEM). The code structure is hardly seen due to the grainy surface of the tablets.

FIG. 4 shows a scanning electron microscopy picture of a pharmaceutical tablet with a datamatrix code structure impressed in the surface. For the SEM image the tablet was coated with 50 nm gold in an evaporation chamber to render the surface conductive.

In still another embodiment the tablets or pills comprise one or more identical predetermined three-dimensional structures as defined above are located on both sides of the pill. This ensures a reliable method of verification, as at least one face of the tablet will be in the direction of the optical detection device. This is particular suitable if tablets are verified through a blister package.

In a further embodiment the tablets or pills comprise two different predetermined three-dimensional structures as defined above on each side of the tablet or pill. This ensures a reliable method to verify the orientation of the table in the package. This is particular suitable if tablets are verified through a blister package. Methods to manufacture embossing or impressing tools for tablets or pill according to this invention are known in the art. Laser writing or e-beam lithography combined with dry etching are two possibilities. EP1958620A1 and WO2007144826A2 disclose another possibility based on photo lithography.

While this detailed description describes a number of preferred embodiments of the present invention, those skilled in the art will understand that these specific details are not to be read into the claims. The invention contemplates, and those skilled in the art will understand, that the various components and parameters described above are subject to a reasonable degree of variation or modification, without departing from the spirit and scope of the invention

We claim:

1. A method for tracking and tracing a tablet or pill located in a package with an optional information sheet, the tablet or pill including a core and a coating enclosing the core, the method comprising:
   detecting a two-dimensional or three-dimensional code structure embossed at an interface between the core and the coating of the tablet or pill using an optical reader which uses parallel optical low-coherence tomography (pOCT) which enables spatial resolution in the micrometer range of the embossed two-dimensional or three-dimensional code structure;
   detecting additional information carrying structures or features on the package or on the information sheet in the package;
   comparing the detected dimensional code structure with the detected additional information; and
   verifying the authenticity of the tablet or pill based on the comparison within one second of when both the dimensional code structure and the additional information have been detected.

2. The method of claim 1, further comprising:
   comparing the detected dimensional code structure with information stored in an external database.

3. The method of claim 1, wherein each of the dimensional code structure on the tablet or pill and the additional information on the package or the information sheet includes authentication information pertaining to the tablet or pill.

4. The method of claim 2,
   wherein the verification of the authenticity of the tablet or pill occurs before the comparison with information stored in the external database.

5. The method of claim 1, wherein the authenticity of the tablet or pill is verified without accessing an external database.

* * * * *